United States Patent
Abbott et al.

(10) Patent No.: US 9,284,264 B2
(45) Date of Patent: Mar. 15, 2016

(54) IONIC LIQUIDS

(75) Inventors: Andrew Peter Abbott, Leicester (GB); Hadi Mohammad Ali Abood, Baghdad (IQ)

(73) Assignee: UNIVERSITY OF LEICESTER, Leicester (GB)

(*) Notice: Subject to any disclaimer, the term of this patent is extended or adjusted under 35 U.S.C. 154(b) by 965 days.

(21) Appl. No.: 13/511,179

(22) PCT Filed: Nov. 25, 2010

(86) PCT No.: PCT/GB2010/002195
§ 371 (c)(1), (2), (4) Date: Sep. 11, 2012

(87) PCT Pub. No.: WO2011/064556
PCT Pub. Date: Jun. 3, 2011

(65) Prior Publication Data
US 2013/0001092 A1   Jan. 3, 2013

(30) Foreign Application Priority Data
Nov. 25, 2009 (GB) .................................. 0920590.7

(51) Int. Cl.
| | | |
|---|---|---|
| C07C 233/05 | (2006.01) | |
| C07C 275/02 | (2006.01) | |
| C25D 3/56 | (2006.01) | |
| C25D 3/66 | (2006.01) | |
| C07C 275/06 | (2006.01) | |
| C25D 3/44 | (2006.01) | |

(52) U.S. Cl.
CPC ............ *C07C 233/05* (2013.01); *C07C 275/02* (2013.01); *C07C 275/06* (2013.01); *C25D 3/44* (2013.01); *C25D 3/665* (2013.01)

(58) Field of Classification Search
None
See application file for complete search history.

(56) References Cited

U.S. PATENT DOCUMENTS

| | | | | |
|---|---|---|---|---|
| 3,725,464 | A * | 4/1973 | De Marco | C07C 271/06 560/166 |
| 4,764,440 | A | 8/1988 | Jones et al. | |
| 5,728,888 | A | 3/1998 | Aumuller et al. | |
| 8,518,298 | B2 * | 8/2013 | Abbott | C25C 3/00 205/234 |
| 8,557,228 | B2 * | 10/2013 | Fitzgerald | A61K 8/26 424/65 |
| 2009/0194426 | A1 * | 8/2009 | Abbott | C25C 3/00 205/234 |
| 2012/0282205 | A1 * | 11/2012 | Pan | A61K 8/26 424/68 |
| 2013/0273442 | A1 * | 10/2013 | Ogumi | H01M 4/9016 429/405 |
| 2013/0288886 | A1 * | 10/2013 | Aduri | H01B 1/122 502/168 |

FOREIGN PATENT DOCUMENTS

| | | |
|---|---|---|
| SU | 535377 | 11/1976 |
| WO | WO-2004/016571 | 2/2004 |
| WO | WO-2004/106287 | 12/2004 |
| WO | WO-2007/003956 | 1/2007 |

OTHER PUBLICATIONS

International Search Report and Written Opinion for PCT/GB2010/002195 dated Sep. 27, 2011.
International Preliminary Report on Patentability issued on PCT/GB2010/002915, mailed Jun. 7, 2012.

* cited by examiner

*Primary Examiner* — Joseph D Anthony
(74) *Attorney, Agent, or Firm* — Foley & Lardner LLP (57) ABSTRACT

There is provided a mixture having a freezing point of up to 100° C. formed by a process comprising the step of contacting: (A) from 1 to 2 equivalents of a compound of formula (I) $AlX_3$ (I) wherein each X independently represents Cl, Br or F; with (B) 1 equivalent of a compound of formula (II) $R^1$—C(O)—N($R^2$)($R^3$) (II) wherein $R^1$ to $R^3$ have meanings given in the description. There is also provided further mixtures containing additional components, as well as methods of using the mixtures in various applications, such as for the electroreduction of the mixtures to produce aluminum metal.

12 Claims, 8 Drawing Sheets

IONIC LIQUIDS

CROSS-REFERENCE TO RELATED APPLICATIONS

This application is a U.S. national stage application of International Application Ser. No. PCT/GB2010/002195, filed on Nov. 25, 2010, and claiming the benefit of the filing date of GB 0920590.7, filed on Nov. 25, 2009, the entire disclosures of which are hereby incorporated by reference for all purposes in their entirety as fully set forth herein.

This invention relates to a new mixture that is a low temperature (e.g. ambient temperature or thereabouts) ionic liquid, as well as to uses for and methods of preparation of such mixtures.

The listing or discussion of a prior-published document in this specification should not necessarily be taken as an acknowledgement that the document is part of the state of the art or is common general knowledge.

Ionic compounds are typically crystalline solids that have a high melting point. These properties of ionic compounds derive from strong electrostatic interactions between ions of opposite charges, which provides a large enthalpic driving force for the formation of ordered lattices (in which lattices the ionic interactions can be maximised).

However, there are certain ion-based systems that remain in the molten state at relatively low temperatures (e.g. about ambient temperature), and are therefore termed "ionic liquids". The fluid state in these systems is maintained, for example, by the use of cations and/or anions that allow for minimisation of the electrostatic interaction between ions of opposite charge (e.g. by increasing the distance of closest possible approach between charge centres).

Ionic liquids have a number of useful and interesting properties. For example, due to their characteristically very low vapour pressure, they represent an attractive alternative to conventional (uncharged) solvent systems, which can produce hazardous vapours. Further, they have particular application as electrolytes or as solvents for ionic compounds (such as metal salts) and thus have utility, for example in electrochemical systems (such as fuel cells, electrochromic devices and photovoltaic devices) and electrochemical processes (such as electrodeposition and electropolishing).

Various ionic liquids deriving from $AlCl_3$ are known. Such liquids can be prepared by reacting a tertiary ammonium halide or quaternary ammonium or phosphonium salt with $AlCl_3$ (as described, for example, in U.S. Pat. Nos. 4,764,440, 5,525,567, 5,731,101, 5,892,124, FR 2 611 700, FR 2 626 572, EP 0 838 447, WO 95/21872).

In the formation of such ionic liquids, reaction with the counter-anion of the ammonium or phosphonium salt converts $AlCl_3$ to anionic species (i.e. to aluminate anions such as $AlCl_4^-$). Such anionic species are more difficult (i.e. require more energy) to reduce to aluminium metal than are equivalent neutral or cationic species containing aluminium.

With certain metals other than aluminium (i.e. Mg, Ca, Cr, Mn, Fe, Co, Ni, Cu, Zn, Ga, Ge, In, Sn, Tl, Pb, Cd, Hg and Y), it is known that ionic liquids can be formed by reacting a metal salt with a "complexing agent". In this instance, the complexing agent acts to solvate anions (by hydrogen bonding) and to coordinate to the metal ion (via a heteroatom having a lone pair of electrons). Such ionic liquids are described in WO 2007/003956.

Due to the strength of bonds between aluminium and halogen atoms (such as chlorine, bromine or fluorine), however, those skilled in the art would not have expected neutral, organic "complexing" agents to be able to form ionic liquids by reaction with aluminium trihalides.

We have now found, surprisingly, that ionic liquids can be formed by reaction between an aluminium trihalide and certain specific organic molecules (amides or ureas).

According to a first aspect of the invention, there is provided a mixture having a freezing point of up to 100° C. formed by a process comprising the step of contacting:

(A) from 1 to 2 equivalents of a compound of formula (I)

wherein each X independently represents Cl, Br or F; with (B) 1 equivalent of a compound of formula (II)

wherein

R$^1$ represents
  C$_{1-4}$ alkyl optionally substituted by one or more F atoms,
  —N(H)R$^4$, R$^4$ represents H or C$_{1-4}$ alkyl optionally substituted by one or more F atoms and R$^2$ and R$^3$ independently represent
  H,
  C$_{1-6}$ alkyl optionally substituted by one or more F atoms or aryl, which mixture is referred to hereinafter as "the mixture of the invention".

Because the mixtures of the invention are liquid at relatively low temperatures and contain ionic species, they can be referred to as ionic liquids.

When used herein, the term "contacting" includes references to bringing the components of the mixture of the invention (including the compound of formula (I) and compound of formula (II)) into contact. This may be achieved, for example, by addition of one component to the other component(s), either with or without active mixing (i.e. physical agitation) of the resulting mixture. As the compounds of formulae (I) and (II) can interact chemically (in that the compound of formula (II) can bond/coordinate to the metal centre in the compound of formula (I) and can also form hydrogen bonds with X$^-$ anions), the term "contacting" also includes references to reacting.

When used herein, the term "equivalent" refers to a molar equivalent. References to "equivalents" are to be construed accordingly.

When used herein, the term "aryl" includes references to C$_{6-10}$ carbocyclic aromatic groups (e.g. naphthyl or, particularly, phenyl groups), which groups may comprise either one or two rings and may be substituted by one or more substituents selected from halo, nitro, C$_{1-4}$ alkyl and C$_{1-4}$ alkoxy, which latter two groups are optionally substituted by one or more F atoms.

The term "halo", when used herein, includes fluoro, chloro, bromo and iodo.

Unless otherwise specified, alkyl and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic.

Embodiments of the invention include those in which:

(1) the 1 to 2 equivalents of the compound of formula (I) comprises a mixture of two or more different compounds of formula (I) which differ in the definition(s) of X;

(2) the 1 equivalent of the compound of formula (II) comprises a mixture of two or more different compounds of formula (II) which differ in the definition(s) of one or more of $R^1$, $R^2$ and $R^3$.

However, particular embodiments of the invention include those in which:
(1) the 1 to 2 equivalents of the compound of formula (I) are formed from a single compound of formula (I) (i.e. a compound having a single definition of X, such as $AlCl_3$);
(2) the 1 equivalent of the compound of formula (II) is formed from a single compound of formula (II) (e.g. acetamide, urea or 1,3-dimethylurea);
(3) the 1 to 2 equivalents of the compound of formula (I) are formed from a single compound of formula (I) (i.e. a compound having a single definition of X, such as $AlCl_3$) and the 1 equivalent of the compound of formula (II) is formed from a single compound of formula (II) (e.g. acetamide, urea or 1,3-dimethylurea).

Further embodiments of the invention include those in which:
(1) each X represents Cl;
(2) $R^1$ represents $C_{1-3}$ alkyl (e.g. methyl) or $-N(H)R^4$;
(3) $R^2$ represents H or $C_{1-3}$ alkyl (e.g. methyl);
(4) $R^3$ represents H;
(5) $R^4$ represents H or $C_{1-3}$ alkyl (e.g. methyl).

Still further embodiments of the invention include those in which:
(1) the compound of formula (I) is $AlCl_3$;
(2) $R^1$ represents methyl, $-NH_2$ or $-N(H)CH_3$;
(3) $R^2$ represents H or methyl;
(4) $R^3$ represents H.

In this respect, particular embodiments of the invention that may be mentioned include those in which the compound of formula (I) is $AlCl_3$ and the compound of formula (II) is 1,3-dimethylurea or, particularly, acetamide or urea.

The freezing point of the mixture, as mentioned above, is up to 100° C., but may, in certain embodiments of the invention, be up to 95, 90, 80, 60, 50, 45, 40, 35, 30 or, particularly, 25, 20, 15 or 10° C. Thus, the freezing point of the mixture may be in the range from −35° C. (or, particularly, −30° C.) to any of the above-mentioned upper limits. In this respect, the freezing point of a mixture is defined as the temperature at which solidification is first observable when the mixture is allowed to cool from a higher temperature.

Due to the ability of ions to migrate through a liquid mixture of the invention, the mixture of the invention is conductive in the liquid state. The conductivity of the mixture of the invention will depend, amongst other things, upon temperature and the specific components of the mixture. However, in a particular embodiment, the mixture of the invention, if liquid at 25° C., has a conductivity at that temperature of any value in the range from 1 to 10,000 microsiemens per centimetre ($\mu S\ cm^{-1}$), such as from 10 to 1000 $\mu S\ cm^{-1}$. In other embodiments of the invention, the mixture of the invention, if liquid at 50° C., has a conductivity at that temperature of any value in the range from 10 to 10,000 $\mu S\ cm^{-1}$, such as from 100 to 2000 $\mu S\ cm^{-1}$.

As mentioned above, the mixture of the invention is formed by contacting 1 (one) equivalent of the compound of formula (II) with from 1 to 2 equivalents of a compound of formula (I). However, particular embodiments of the invention relate to mixtures formed by contacting 1 equivalent of the compound of formula (II) with 1 or 2 equivalents of a compound of formula (I).

The process for forming the mixture of the invention can be conducted under a variety of conditions and either in the presence or absence of substances other than the compound(s) of formula (I) and the compound(s) of formula (II).

Thus, embodiments of the invention include those in which the mixture is formed by contacting the compound(s) of formula (I) and the compound(s) of formula (II) at ambient temperature (e.g. from 15 to 30° C.). As contacting the compound(s) of formula (I) with the compound(s) of formula (II) may result in an exothermic reaction, the resulting mixture may, in some embodiments, be cooled (e.g. using conventional cooling methods) to prevent overheating. However, in other embodiments of the invention, the resulting mixture is not actively cooled but is instead allowed to cool gradually to ambient temperature. In still further embodiments of the invention, the mixture formed by contacting the compound(s) of formula (I) with the compound(s) of formula (II) is, either before or after cooling to ambient temperature, heated to above ambient temperature (e.g. to a temperature of from 80 to 150° C., such as to a temperature of about 100° C.) in order to ensure complete conversion to a mixture of the invention.

Further, certain embodiments of the invention relate to a mixture having a freezing point of up to 100° C. formed by a process consisting essentially of the step of contacting from 1 to 2 equivalents of a compound of formula (I) with 1 equivalent of a compound of formula (II). In these embodiments, the components of the mixture, the ratios of those components, and the conditions under which the mixture may be formed are as described in relation to the above-mentioned embodiments of the invention.

The term "consisting essentially", when used herein in relation to a process for forming a mixture, refers to a process consisting of the step(s) described but no prior or subsequent steps that are not described or cannot be inferred to be required.

In addition to the above, further embodiments of the invention relate to mixtures formed by contacting the compounds of formulae (I) and (II) in the substantial absence of:
(i) liquids other than the compound(s) of formula (II); and/or
(ii) organic compounds other than the compound(s) of formula (II).

Still further embodiments of the invention relate to mixtures formed by contacting the compounds of formulae (I) and (II) in the substantial absence of any materials other than the compounds of formulae (I) and (II).

Thus, embodiments of the invention relate to mixtures consisting essentially of compounds of formulae (I) and (II) and/or reaction product(s)/adduct(s) formed from those components.

The term "substantial absence", when used herein, refers to the presence of at most 10% by weight of the material or substance in question, such as at most 5 or, particularly, 1, 0.1 or 0.01% by weight of said material or substance. In this instance, percentage by weight is calculated by reference to the weight of the resulting mixture of the invention (or the combined weight of the components used to form said mixture).

The term "organic compound", when used herein, refers to any chemical compound (other than carbon, oxides of carbon, or acids or salts of (bi)carbonate, cyanide, cyanate, thiocyanate or fulminate), whose molecules contain carbon.

The mixtures of the invention described herein are, in particular embodiments of the invention, formed under an inert atmosphere (e.g. under an atmosphere of argon or, particularly, nitrogen). In these embodiments, the mixtures of the invention may, in particular, be formed using anhydrous reagents (compound(s) of formula (I) and salt(s) of formula (II)) and gases (e.g. argon or nitrogen). In this context, the term "anhydrous" includes references to reagents and gases that comprise less than 0.5% by weight of water (e.g. less than 0.4, 0.3, 0.2, 0.1 or 0.05% by weight of water).

The invention also relates to mixtures comprising more materials than just the compounds of formulae (I) and (II) (and their reaction product(s)/adduct(s)). Thus, a further aspect of the invention relates to a mixture formed by a process comprising (or, alternatively, consisting essentially of) the steps of:

(1) contacting from 1 to 2 equivalents of a compound of formula (I), as hereinbefore defined, with 1 equivalent of a compound of formula (II), as hereinbefore defined; and
(2) contacting the mixture so formed with an additive.

The mixture so formed is also referred to hereinafter as "the mixture of the invention".

Embodiments of this aspect of the invention also include those in which the mixture formed in step (2) has a freezing point of up to 100° C. (or any of the other freezing point values or ranges described above in relation to the mixture of the invention).

Additives that may be mentioned in respect of this aspect of the invention include those modifying electrochemical properties (e.g. conductivity or redox potentials) or physiochemical properties (e.g. viscosity or colour) of the mixtures of the invention. Specific additives that may be mentioned therefore include: diluents (to decrease viscosity), such as diluents that are organic compounds that do not contain any oxygen atoms (e.g. toluene); electrolytes (to increase conductivity), such as lithium chloride; and brighteners (to modify the reduction potential of the metal or absorb at the electrode interface), such as nitrogen-donor ligands (e.g. ethylene diamine).

The mixtures according to the invention may be utilised for a wide range of applications. Thus, further aspects of the invention relate to the use of a mixture of the invention as a solvent, as an electrolyte, as a reagent or as a catalyst.

When used as a solvent, the mixtures of the invention can be used, for example:
(i) to dissolve metal-containing ionic compounds (e.g. metal salts and metal oxides);
(ii) as solvent systems for inorganic and organic compounds;
(iii) as solvent systems in which chemical reactions are performed; or
(iv) as solvent systems into which compounds are extracted from an immiscible fluid phase.

Thus, a further aspect of the invention relates to a method of forming a solute, which method comprises dissolving the solute in a mixture of the invention.

When used as an electrolyte, the mixtures of the invention can be used, for example:
(i) as electrolytes in electrochemical devices (such as batteries or fuel cells), in photovoltaic or electrochromic devices; or
(ii) as electrolytes/solvents for electrochemical reactions (e.g. electrochemical deposition, electropolishing or electro-refining).

Thus, a further aspect of the invention relates to a method of carrying out an electrolytic reaction (such as an electropolishing reaction or, particularly, an electroplating reaction), which method comprises employing as a solvent and/or as an electrolyte for the electrolytic reaction a mixture of the invention.

Due to the presence of trivalent aluminium ions in the mixtures of the invention, those mixtures may (as mentioned above) be employed as catalysts or as chemical reagents.

When used as a catalyst, the mixtures of the invention can be used, for example as a Lewis acid catalyst in reactions such as:

(i) a Friedel-Crafts reaction (reaction between aromatic groups and alkyl or acyl halides);
(ii) a cycloaddition reaction (e.g. a Diels Alder reaction (coupling of a diene to a dienophile) or 1,3-dipolar cycloaddition);
(iii) a Fischer indole synthesis (cyclisation of aryl hydrazones);
(iv) polymerisation of an olefin;
(v) a Mukaiyama aldol addition (addition of a silyl enol ether to an aldehyde);
(vi) a McMurry reaction (coupling of two aldehyde or ketone groups to form an alkene); and
(vii) a Baylis-Hillman reaction (coupling of an aldehyde and an alkene having an electron-withdrawing group attached to an unsaturated C-atom of the alkene functional group).

Thus, a further aspect of the invention relates to a method of catalysing a reaction requiring catalysis by a Lewis acid (e.g. a Friedel-Crafts reaction, a Diels Alder reaction, a Fischer indole synthesis or polymerisation of an olefin), said method comprising the step of contacting the reagent or reagents for the reaction with a mixture of the invention.

In addition to the above, a particular application for the mixture of the invention is in the electrodeposition of aluminium.

Thus, a still further aspect of the invention relates to a method of electrodepositing aluminium metal onto a conductive substrate, said method comprising the steps of:
(a) contacting the substrate and a counter electrode with a mixture of the invention; and
(b) electrolysing the mixture by applying a reducing potential to the substrate, relative to the counter electrode.

In a different aspect of the invention, there is provided a method of electrodepositing onto a conductive substrate an alloy of aluminium with another metal, said method comprising the steps of:
(a) contacting the substrate and a counter electrode with a mixture of the invention containing an additive that comprises, in a positive oxidation state, a metal other than aluminium; and
(b) electrolysing the mixture by applying a reducing potential to the substrate, relative to the counter electrode.

In relation to the above-described electrodeposition methods, the conductive substrate may be any suitable solid, conductive material, such as steel, copper, platinum, gold, nickel or aluminium.

Further, the reducing potential applied to the conductive substrate may be, for example, a constant potential. Alternatively, the deposition can be achieved by utilising a constant current. In either instance, the potential applied to the conductive substrate may be, for example, any potential between $-0.5$ V and $-2.5$ V (e.g. between $-1.0$ V and $-2.5$ V, such as between $-1.5$, $-1.6$, $-1.7$, $-1.8$, $-1.9$ or $-2.0$ V and $-2.5$ V) relative to an Ag wire reference electrode immersed in the mixture being electrolysed.

The temperature at which the above-described electrodeposition methods are conducted may be, for example, any temperature from 0 to 200° C. (e.g. from 25 to 160° C., such as from 25 to 125, 100, 80, 70, 60 or 50° C.).

In particular embodiments of the invention, the electrodeposition in the above-described electrodeposition methods is conducted under an inert atmosphere (e.g. under an atmosphere of argon or, particularly, nitrogen). In these embodiments, the gas(es) (e.g. argon or nitrogen) used to form the inert atmosphere are anhydrous. In this context, the term "anhydrous" includes references to gases that comprise less than 0.5% by weight of water (e.g. less than 0.4, 0.3, 0.2, 0.1 or 0.05% by weight of water).

Mixtures of the invention may have the advantage that, compared to ionic mixtures of the prior art that are liquid at low temperatures, they are easier and/or cheaper to prepare, have a lower freezing point, are less viscous, are more conductive, are less dense and/or have a lower surface tension.

Mixtures of the invention may have the advantage that they represent a "stabilised" form of the compound of formula (I) (such as $AlCl_3$). In particular, the mixtures of the invention retain many of the properties of the isolated compound of formula (I) (such as Lewis acidity), but have reduced sensitivity to air and/or water. Thus, mixtures of the invention may have the advantage that, compared to isolated compounds of formula (I), they are much easier and/or safer to handle and/or store (e.g. they have a reduced need for use of strictly anhydrous conditions for use and/or storage). Mixtures of the invention may also possess such advantages relative to known ionic liquids based upon aluminium trihalides (e.g. ionic liquids based upon the mixture of $AlCl_3$ with either an imidazolium salt (such as 1-methyl-3-ethylimidazolium chloride) or a pyridinium salt (such as 1-butylpyridinium chloride).

Other advantages that mixtures of the invention may possess is that they provide a simple, low temperature system from which electrodeposition or electroplating of aluminium metal (or alloy) may be obtained.

Further, due to the mild conditions employed, the mixtures of the invention may provide the advantage that the aluminium metal or alloy can be produced with low energy consumption and/or with a reduced need for high temperature containment materials.

Mixtures of the invention may also have the advantage that they are able to act as catalysts in chemical reactions.

EXAMPLES

General Experimental Procedures

Samples of $AlCl_3$ (99%), acetamide (99%), urea (99%) and dimethylurea (99%) were obtained from Aldrich.

Preparation of mixtures of the invention (ionic liquids) was assumed to be complete when the formation of a homogeneous phase was observed.

The freezing point of the mixtures of the invention can be determined by cooling the mixtures (e.g. at a rate of 1° C. $min^{-1}$) and establishing the temperature (the freezing point) at which the first solid is observed to form, or by using differential scanning calorimetry (DSC).

Where relevant, the conductivity of mixtures was measured using a Jenway 4071 conductivity meter, with temperature and conductivity probes (probe cell constant 1.01 $cm^{-1}$).

Cyclic voltammetry experiments were performed using an Echo Chemie Autolab PGSTAT12 potentiostat, at ambient room temperature (i.e. at around 20° C.), and using a platinum working electrode (1 mm diameter), platinum counter electrode and silver wire quasi-reference electrode.

Surface analysis was carried out using scanning electron microscopy (Philips XL30 ESEM) and energy dispersive analysis by X-rays (EDX).

All NMR spectra were recorded on a Bruker ARX 300 spectrometer at ambient temperature in the neat liquid.

Fast Atom Bombardment (FAB) mass spectra were recorded on a Kratos Concept 1H using xenon with the neat liquid.

Infrared (IR) spectra were recorded using a Perkin Elmer Spectrum One FT-IR with ATR attachment and were measured in units of $cm^{-1}$.

Viscosity was determined using a Brookfield DV-E viscometer.

Examples

Example 1

Figure 1A:
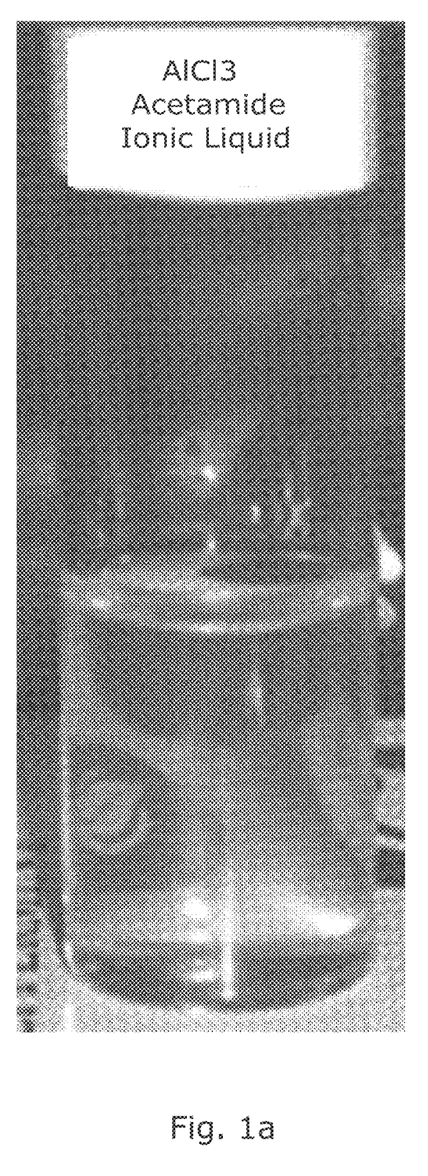
FIG. 1a shows a mixture of the invention formed by reaction between $AlCl_3$ and acetamide (in a 1:1 molar ratio), as described in Example 1.

Aluminium chloride (2.1 g, 15.75 mmol) was mixed in a 1:1 mole ratio with acetamide (0.93 g, 15.75 mmol) in test tube under blanket of dry nitrogen gas. The aluminium chloride reacted immediately after complete mixing was achieved, evolving a small amount of white fumes and forming clear liquid. The reaction was exothermic and the liquid was left to cool gradually to room temperature, producing clear, pale yellow, free-flowing liquid (see FIG. 1a).

The resulting liquid was found to be miscible with some organic solvents (e.g. toluene). It was also found, by visual observation of the relative rates of hydrolysis, to be less sensitive to air than chloroaluminate ionic liquids formed from aluminium chloride and either 1-ethyl-3-methylimidazolium or 1-butylpyridinium chloride.

Analysis at 25° C.
  Density: 1.4 to 1.5 $g/cm^3$
  Conductivity: 0.804 $mScm^{-1}$
  Viscosity: 60 Cp
Conductivity

| Temperature (° C.) | Conductivity (mS) |
|---|---|
| 20 | 0.672 |
| 25.5 | 0.855 |

-continued

| Temperature (° C.) | Conductivity (mS) |
|---|---|
| 30 | 0.983 |
| 35 | 1.158 |
| 40 | 1.319 |
| 44.5 | 1.45 |
| 50 | 1.64 |
| 55 | 1.798 |
| 60 | 1.98 |
| 64 | 2.22 |
| 71 | 2.42 |
| 73 | 2.51 |

Viscosity

| Temperature (° C.) | Viscosity (Cp) |
|---|---|
| 20 | 70 |
| 25 | 60 |
| 30 | 48 |
| 35 | 42 |
| 40 | 36 |
| 45 | 31 |

DSC Analysis

Figure 2:
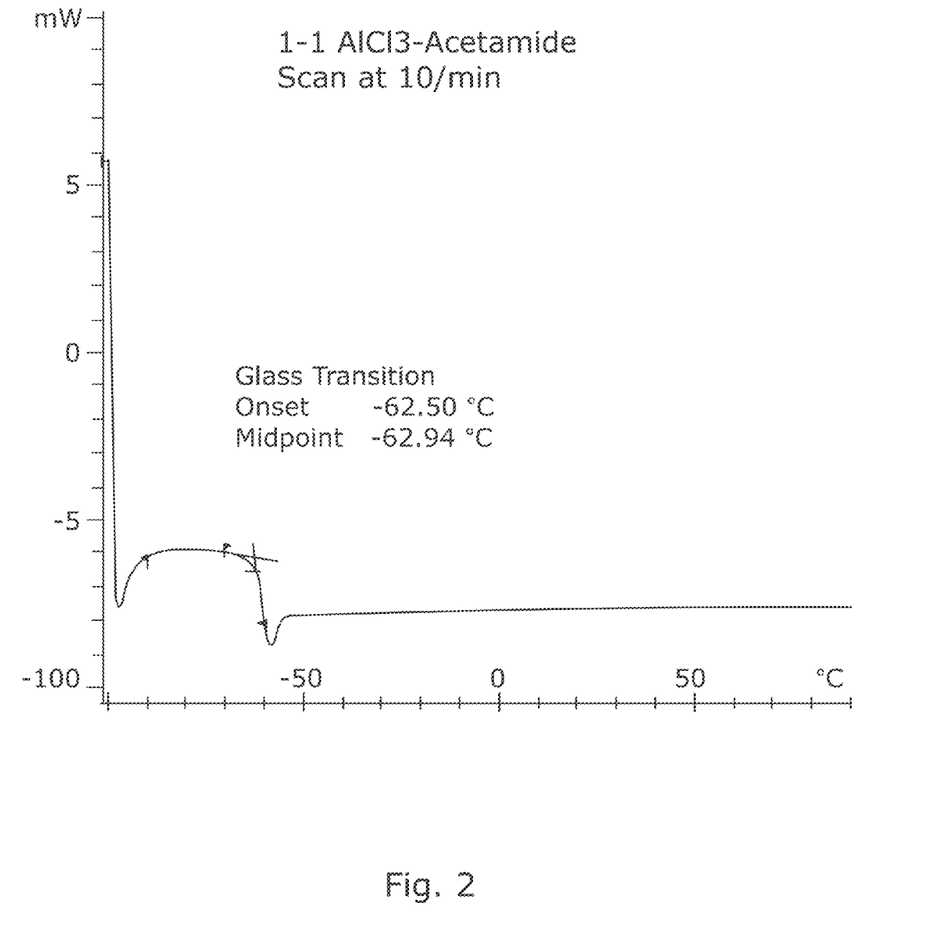
FIG. 2 shows the differential scanning calorimetry (DSC) trace (obtained at a scan rate of 10° C./min) for the mixture of Example 1, which trace exhibits a glass transition with an onset at −62.5° C. and a midpoint at −62.94° C.

When analysed by DSC using a scan rate of 10° C./min (see FIG. 2), the liquid showed a glass transition temperature around −63° C. Further, the liquid appeared to be chemically stable up to about 100° C.

Infrared Analysis

IR analysis showed vibration peaks indicating interaction of aluminium trichloride with acetamide, probably through the oxygen of the carbonyl group, thereby influencing the N—H, $NH_2$, C=O and the C—H vibrations as compared with pure acetamide in its solid form. The table below shows the peaks for solid acetamide and the peaks for $AlCl_3$/acetamide liquids, the latter in both 1:1 (Example 1) and 2:1 (Example 2) ratios.

| Solid Acetamide | | $AlCl_3$/Acetamide Liquid | | Band |
|---|---|---|---|---|
| Vibration ($cm^{-1}$) | Intensity | Vibration ($cm^{-1}$) | Intensity | assignment |
| 3300 | S | 3435 | M | N—H |
| 3151 | Vs | 3361 | M | N—H |
| 2818 | W | 3292 | M | C—H |
| 1673 | VS | 1662 | VS | C=O |
| 1631 | Vs | 1557 | S | C=O |
| 1459 | M | 1494 | S | C—H |
| 1393 | VS | 1410 | M | C—H |
| 1357 | S | 1368 | M | C—H |
| 1149 | VS | 1129 | M | $NH_2$ |
| 1046 | W | 1016 | W | Chain |
| 1006 | W | 902 | M | chain |
| 873 | S | — | — | chain v |

Key:
W = weak;
M = medium;
S = strong;
VS = very strong.

FAB-MS Analysis

Figure 3A:
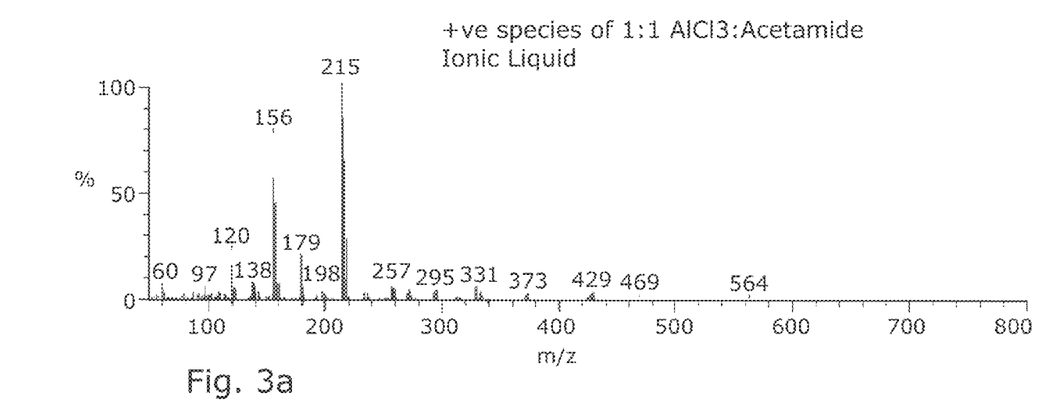
FIG. 3a shows the FAB-MS spectrum (positive mode) for the mixture of Example 1.
Figure 3B:
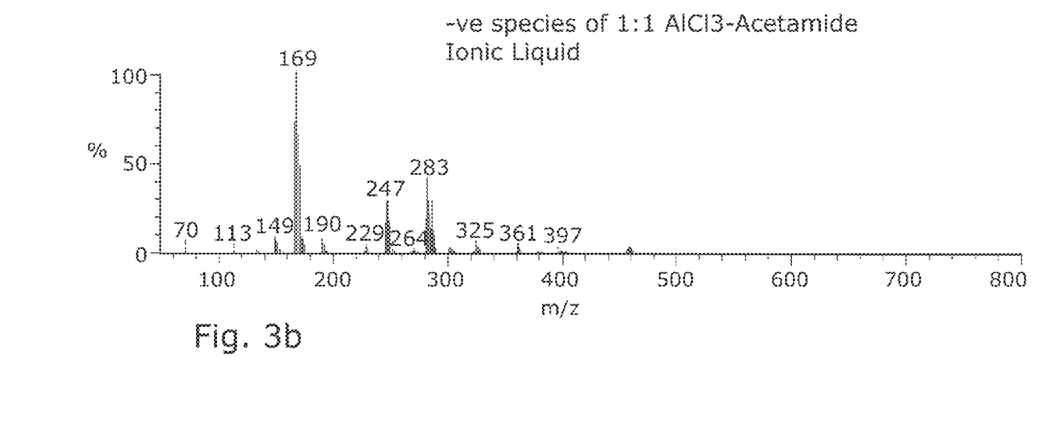
FIG. 3b shows the FAB-MS spectrum (negative mode) for the mixture of Example 1.

The liquid of Example 1 was examined by FAB-MS in both positive and negative modes (see FIGS. 3a and 3b). An interpretation of the peaks observed is provided in the tables below (in which Ac=acetamide).

| Positive Mode | | |
|---|---|---|
| Relative Peak intensity (%) | m/z | Ions |
| 100 | 215 | $[AlCl_2(Ac)_2]^{+1}$ |
| 50 | 156 | $[AlCl_2(Ac)]^{+1}$ |
| 20 | 179 | $[AlCl(Ac)_2]^{+1}$ |
| 15 | 120 | $[AlCl(Ac)]^{+1}$ |

| Negative Mode | | |
|---|---|---|
| Relative Peak intensity (%) | m/z | Ions |
| 100 | 169 | $[AlCl_4]^{-1}$ |
| 50 | 283 | $[Cl_8]^{-1}$ |
| 30 | 247 | $[Cl_7]^{-1}$ |
| 5 | 301 | $[Al_2Cl_7]^{-1}$ |

Figure 4:
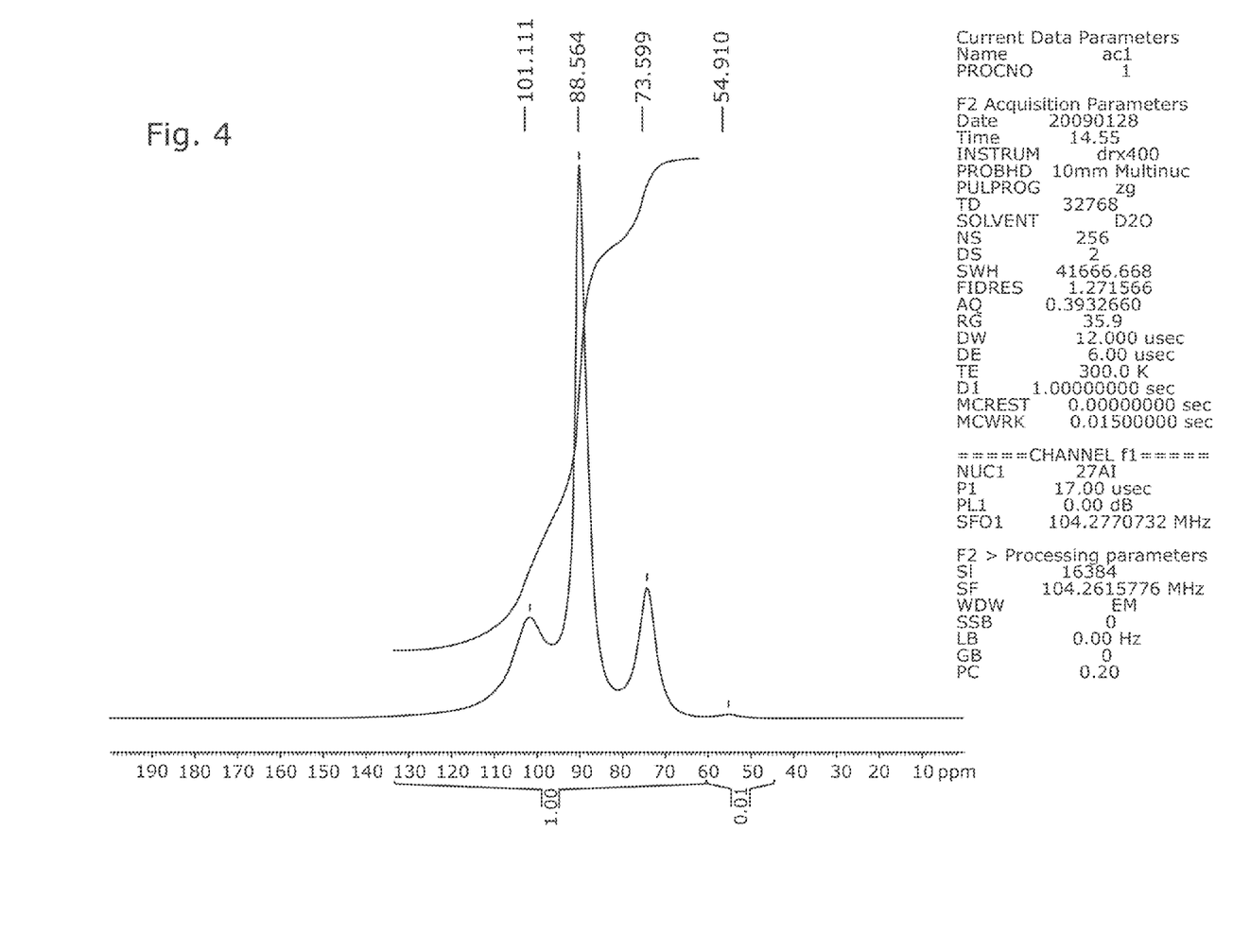
FIG. 4 shows the $^{27}Al$ NMR spectrum for the mixture of Example 1.

$^{27}$Al NMR Analysis $^{27}$Al NMR analysis of the liquid of Example 1 indicated the presence of four different aluminium species in the liquid (see FIG. 4).

Example 2

Under analogous conditions to those described in Example 1 above, aluminium chloride (2.1 g, 15.75 mmol) was mixed with acetamide (0.46 g, 7.8 mmol), making the mole ratio of $AlCl_3$: acetamide approximately 2:1. The liquid obtained after allowing the mixture to cool to room temperature was again free-flowing and pale yellow in colour.

DSC Analysis

When analysed by DSC using a scan rate of 10° C./min, the liquid showed a glass transition temperature around −64° C.

Infrared Analysis

See the table in Example 1 above.

Example 3

Under analogous conditions to those described in Example 1 above, aluminium chloride (4.3 g, 32.25 mmol) was mixed in a test tube with urea (1.93 g, 32.13 mmol) in approximately a 1:1 mole ratio. Mixing the components produced a sudden, exothermic reaction, involving the evolution of a small amount of white fumes and the formation of a yellow liquid. When this liquid was left to cool to less than 20° C., it became more viscous than the liquid of either of Examples 1 and 2.

Figure 1B:
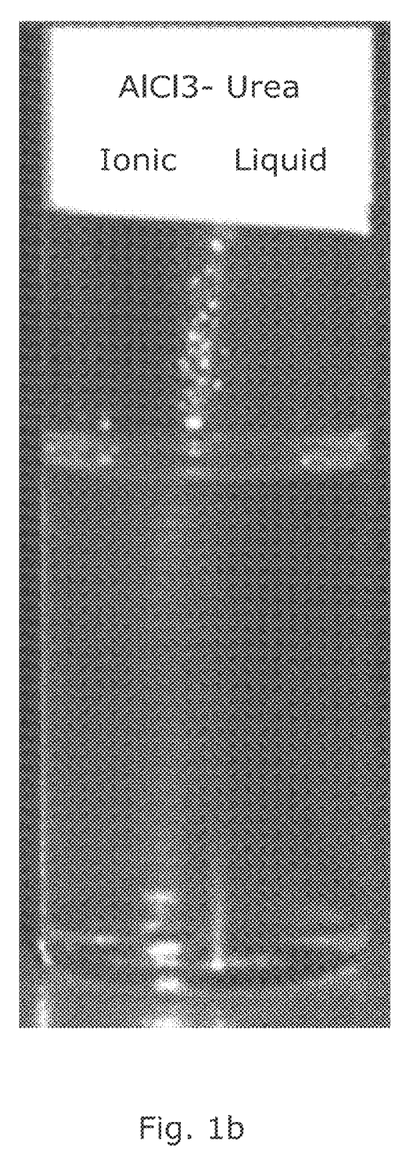
FIG. 1b shows a mixture of the invention formed by reaction between $AlCl_3$ and urea (in a 1:1 molar ratio), as described in Example 3.

The resulting liquid (see FIG. 1b) was found to be miscible with some organic solvents (e.g. toluene). Also, it was determined, by visual observation of the relative rates of hydrolysis, to be less sensitive to air than chloroaluminate ionic liquids formed from aluminium chloride and either 1-ethyl-3-methylimidazolium or 1-butylpyridinium chloride.

DSC Analysis

Figure 5:
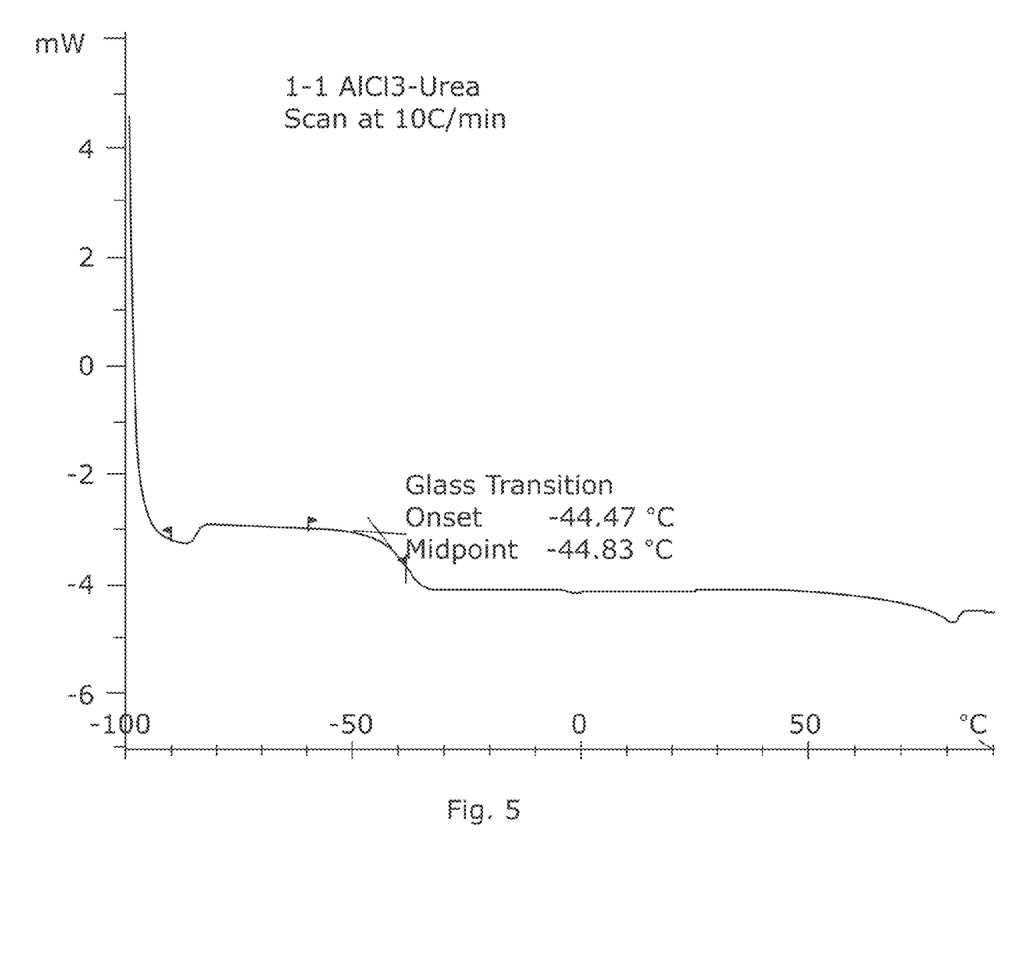
FIG. 5 shows the DSC trace (obtained at a scan rate of 10° C./min) for the mixture of Example 3, which trace exhibits a glass transition with an onset at −44.47° C. and a midpoint at −44.83° C.

When analysed by DSC using a scan rate of 10° C./min (see FIG. 5), the liquid showed a glass transition temperature around −44° C.

Infrared Analysis

IR analysis showed vibration peaks indicating a strong interaction of aluminium with urea, probably through the oxygen of the carbonyl group. It also showed the formation of a new vibration energy at 2272 $cm^{-1}$. The table below shows the peaks for solid urea and the peaks for $AlCl_3$/urea liquids, the latter in both 1:1 (Example 3) and 2:1 (Example 4) ratios.

| Solid Urea | | AlCl₃/Urea Liquid | | Band |
|---|---|---|---|---|
| Vibration (cm⁻¹) | Intensity | Vibration (cm⁻¹) | Intensity | assignment |
| 3429 | Vs | 3484 | S | N—H |
| 3329 | Vs | 3378 | S | N—H |
| — | — | 2272* | S | |
| | | 2340** | M | |
| 3255 | Vs | 3255 | W | N—H |
| 1676 | Vs | 1637 | VS | C=O |
| 1590 | Vs | 1560 | VS | C=O |
| 1540 | M | 1523 | S | NH2 |
| 1460 | Vs | 1408 | S | C—N |
| 1149 | Vs | 1156 | S | NH2 |
| 1046 | W | 1056 | W | C—N |
| 1003 | W | — | — | — |
| 787 | W | 756 | W | chain |

Key:
W = weak;
M = medium;
S = strong;
VS = very strong.
*Liquid formed from a 1:1 ratio of AlCl₃:urea (see Example 3)
**Liquid formed from a 2:1 ratio of AlCl₃:urea (see Example 4)

FAB-MS Analysis

Figure 6A:
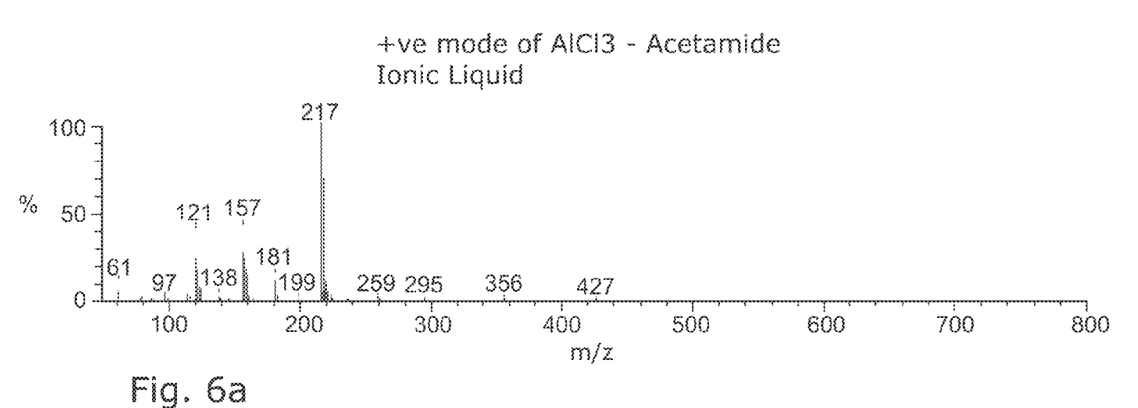
FIG. 6a shows the FAB-MS spectrum (positive mode) for the mixture of Example 3.
Figure 6B:
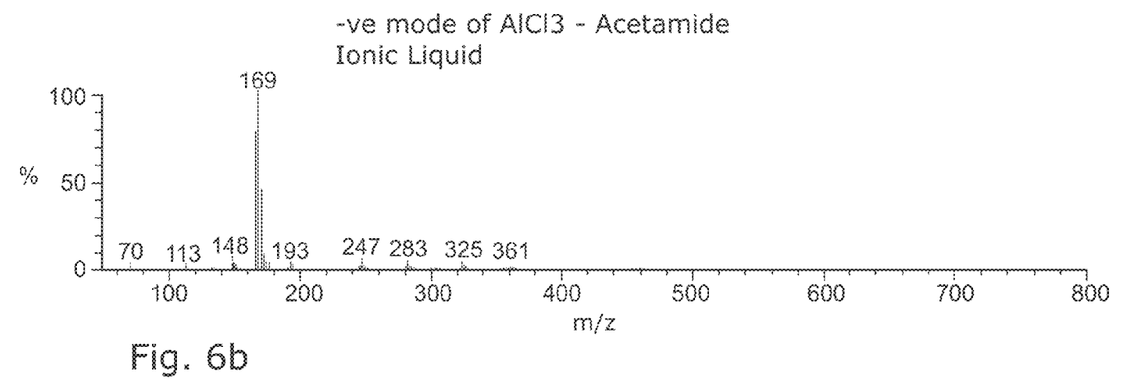
FIG. 6b shows the FAB-MS spectrum (negative mode) for the mixture of Example 3.

The liquid of Example 3 was examined by FAB-MS in both positive and negative modes (see FIGS. 6a and 6b). An interpretation of the peaks observed is provided in the tables below (in which U=urea).

| Positive Mode | | |
|---|---|---|
| Relative Peak intensity (%) | m/z | Ions |
| 100 | 217 | $[AlCl_2(U)_2]^{+1}$ |
| 30 | 157 | $[AlCl_2(U)]^{+1}$ |
| 25 | 121 | $[AlCl(U)]^{+1}$ |
| 10 | 181 | $[AlCl(U)_2]^{+1}$ |

| Negative Mode | | |
|---|---|---|
| Relative Peak intensity (%) | m/z | Ions |
| 100 | 169 | $[AlCl_4]^{-1}$ |
| 7 | 247 | $[Cl_7]^{-1}$ |
| 3 | 301 | $[Al_2Cl_7]^{-1}$ |

Example 4

Under analogous conditions to those described in Example 1 above, aluminium chloride (3.5 g, 26.25 mmol) was mixed in a test tube with urea (0.788 g, 13.1 mmol) in approximately a 2:1 mole ratio. Mixing of the components again resulted in an exothermic reaction and the evolution of small amount of white fumes. However, when the liquid was cooled to room temperature it turned to a glassy solid with many solid particulates. The resulting glassy solid was heated to around 100° C., at which temperature it changed to a liquid. This yellow liquid did not solidify upon cooling to room temperature again, but instead retained its liquid consistency.

DSC Analysis

When analysed by DSC using a scan rate of 10° C./min, the liquid showed a glass transition temperature around −43° C.

Infrared Analysis

See the table in Example 3 above.

Reference Example 5

Under analogous conditions to those described in Example 1 above, aluminium chloride was mixed in a test tube with urea in a 3:1 mole ratio of aluminium chloride to urea. Mixing the components again produced an exothermic reaction and a liquid. However, when this liquid was left to cool it solidified (at a temperature above room temperature). Further, the resulting solid did not liquefy even when heated to 100° C.

Reference Example 6

Under analogous conditions to those described in Example 1 above, aluminium chloride was mixed in a test tube with urea in a 4:1 mole ratio of aluminium chloride to urea. The reaction between the components ultimately resulted in a solid material similar to that observed in Reference Example 5.

Reference Example 7

Under analogous conditions to those described in Example 1 above, aluminium chloride (2.0 g, 15 mmol) was mixed in a test tube with choline chloride (1.05 g, 7.5 mmol) in approximately a 2:1 mole ratio. Although mixing the components produced an exothermic reaction, no liquid was formed. Further, when the resulting solid mixture was heated to 150° C., it did not liquefy.

Reference Example 8

Under analogous conditions to those described in Example 1 above, aluminium chloride (2.3 g, 17.25 mmol) was mixed in a test tube with benzamide (1.04 g, 8.58 mmol) in approximately a 2:1 mole ratio. The resulting solid mixture did not liquefy even upon heating to 150° C.

Reference Example 9

Aluminium chloride (2.5 g, 18.75 mmol) was mixed in a Schlenk tube under a nitrogen atmosphere with ethylene glycol (0.5 g, 8.05 mmol) in approximately a 23:10 mole ratio either by adding ethylene glycol to aluminium chloride or vice versa. Mixing the components resulted in the sudden evolution of large amount of white fumes, which only ceased when addition of components was complete. The resulting mixture was a colourless solid material, which did not liquefy even upon heating to 100° C.

Example 10

A sample of the ionic liquid according to Example 1 can be protected from air if covered with a layer of liquid alkane. For example, covering the ionic liquid of Example 1 with a layer of decane stabilised the liquid to degradation (as determined by NMR analysis) for one day, after which the ionic liquid changed colour to brown (the colour change starting at the interface with the layer of decane). No colour change was observed in the decane layer.

Example 11

A sample of the ionic liquid according to Example 3 can be protected from air if covered with a layer of liquid alkane. For example, covering the ionic liquid of Example 3 with a layer of decane stabilised the liquid to degradation (as determined by NMR analysis) for one month.

Example 12

Aluminium chloride (0.92 g, 6.9 mmol) was mixed with 1,3-dimethylurea (0.304 g, 3.45 mmol) in a 2:1 mole ratio in a test tube under blanket of dry nitrogen gas. Upon complete mixing of the components, an immediate reaction took place, evolving small amount of white fume and forming clear liquid. The reaction was exothermic and the liquid was left to cool gradually to room temperature producing clear, pale yellow liquid.

Example 13

Under analogous conditions to those described in Example 12 above, aluminium chloride (0.884 g, 6.6 mmol) was mixed in a test tube with 1,3-dimethylurea (0.584 g, 6.6 mmol) in a 1:1 mole ratio. The liquid obtained after allowing the mixture to cool to room temperature was free-flowing and pale yellow in colour.

Example 14

Figure 7:
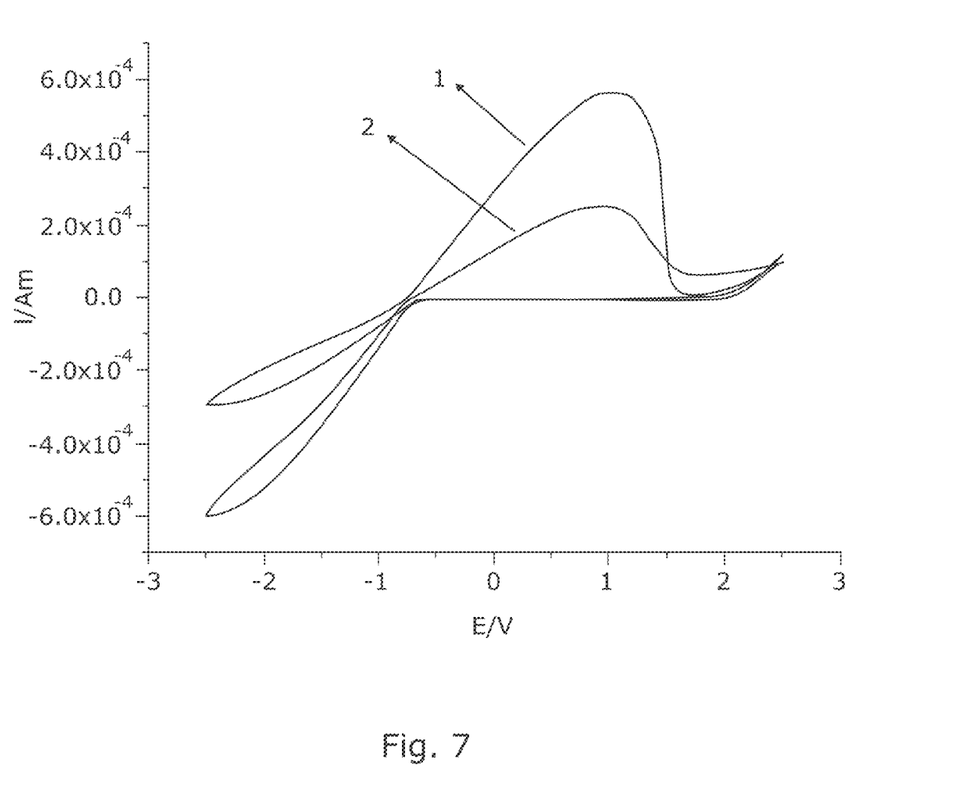
FIG. 7 shows superimposed cyclic voltammograms of the mixture of Example 2 (labelled "1") and the mixture of Example 4 (labelled "2").

Cyclic voltammograms were recorded at room temperature of samples prepared from the liquids of Examples 2 and 4 above. The voltammograms are depicted in FIG. 7 and show peaks for deposition and oxidation of aluminium.

Example 15

The electrodeposition of aluminium can be achieved by, at a temperature from ambient (i.e. room temperature) to about 150° C., applying a constant voltage or constant current across two electrodes immersed in ionic liquids according to the invention, as described above.

Figure 8A:
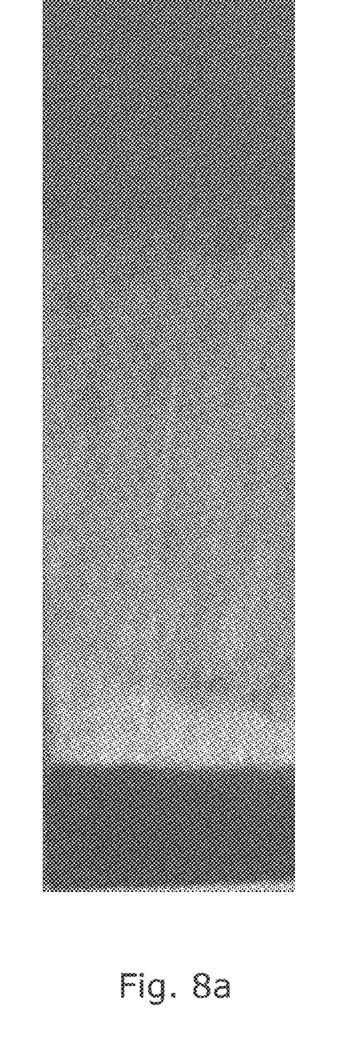
FIG. 8a shows aluminium deposition on a copper cathode from a mixture according to Example 2 (surface shown is that facing the aluminium anode employed in the electrodeposition experiment described in Example 15).
Figure 8B:
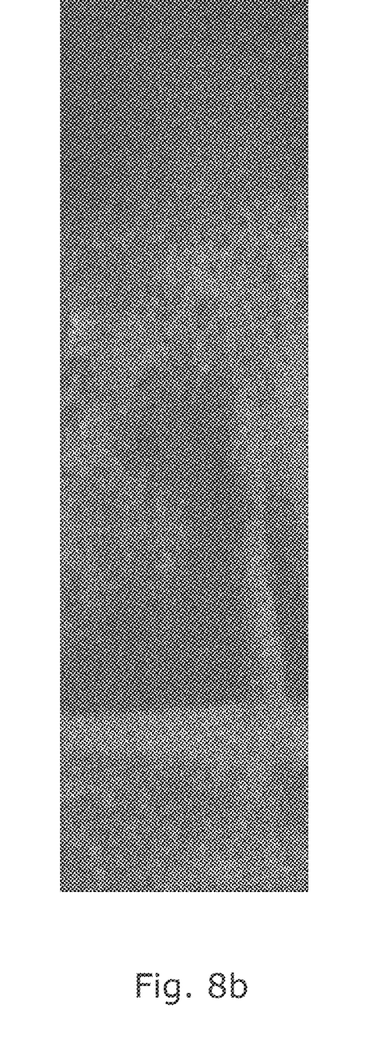
FIG. 8b shows aluminium deposition on a copper cathode from a mixture according to Example 2 (surface shown is that facing away from the aluminium anode employed in the electrodeposition experiment described in Example 15).

For example, electrodeposition of aluminium on copper was conducted by immersing aluminium anode and copper cathode at room temperature into ionic liquid that was freshly prepared as in Example 2 and covered with decane as in Example 10. The deposition was achieved by applying a constant current of 2 mA/cm² when a stable voltage (0.4 volt) was recorded for one hour. The copper cathode was covered after one hour by a smooth black coating that was well adhered to the surface facing the anode, and by a grey matt coating on the reverse face of the cathode (see FIGS. 8*a* and 8*b*).

The coatings were examined by SEM and EDX and found to contain only aluminium.

Example 16

Electrodeposition of aluminium on copper was conducted by immersing aluminium anode and copper cathode at room temperature into ionic liquid that was freshly prepared as in Example 4 and covered with decane as in Example 11. The deposition was achieved by applying a constant current of 2 mA/cm² when an increase voltage up to 23 volt was recorded after 10 minutes. The copper cathode was covered after 10 minutes by a smooth, well-adhered black coating on the surface facing the anode, and by a grey matt coating on the reverse face of the cathode.

The coatings were examined by SEM and EDX and found to contain only aluminium.

The invention claimed is:

1. A mixture having a freezing point of up to 100° C. formed by a process comprising the step of contacting:
    (A) from 1 to 2 equivalents of a compound of formula (I)

wherein each X independently represents Cl, Br or F; with
    (B) 1 equivalent of a compound of formula (II)

wherein:
    $R^1$ represents
        $C_{1-4}$ alkyl optionally substituted by one or more F atoms,
        —N(H)$R^4$;
    $R^4$ represents H or $C_{1-4}$ alkyl optionally substituted by one or more F atoms; and
    $R^2$ and $R^3$ independently represent
        H,
        $C_{1-6}$ alkyl optionally substituted by one or more F atoms or aryl.

2. The mixture of claim 1, wherein the compound of formula (I) is $AlCl_3$.

3. The mixture of claim 1, wherein:
    $R^1$ represents methyl, —$NH_2$ or —N(H)$CH_3$;
    $R^2$ represents H or methyl; and
    $R^3$ represents H.

4. The mixture of claim 3, wherein the compound of formula (II) is acetamide or urea.

5. The mixture of claim 1, wherein the process is conducted in the substantial absence of organic compounds other than the compound of formula (II).

6. The mixture of claim 1, wherein the mixture has a freezing point of up to 80° C.

7. A mixture formed by a process comprising:
    contacting from 1 to 2 equivalents of a compound of formula (I)

with 1 equivalent of a compound of formula (II)

to form a mixture;
    wherein:
        each X independently represents Cl, Br or F;
        $R^1$ is $C_{1-4}$ alkyl optionally substituted by one or more F atoms, or —N(H)$R^4$;
        $R^4$ is H or $C_{1-4}$ alkyl optionally substituted by one or more F atoms; and
        $R^2$ and $R^3$ independently represent H, $C_{1-6}$ alkyl optionally substituted by one or more F atoms, or aryl; and
    contacting the mixture with an additive.

8. The mixture of claim 7, wherein the additive is a diluent, an electrolyte, or a brightener.

9. A composition comprising the mixture of claim 1, wherein the mixture is a solvent, an electrolyte, a reagent, or a catalyst.

10. A method of carrying out an electrolytic reaction, which method comprises employing as a solvent and/or as an electrolyte for the electrolytic reaction mixture of claim 1.

11. A method of electrodepositing aluminum metal onto a conductive substrate, said method comprising:

contacting the substrate and a counter electrode with the mixture of claim 1; and electrolysing the mixture by applying a reducing potential to the substrate, relative to the counter electrode.

12. A method of electrodepositing onto a conductive substrate an alloy of aluminum with a metal other than aluminum, said method comprising the steps of:
- (a) contacting the substrate and a counter electrode with the mixture of claim 7, wherein the additive comprises, in a positive oxidation state, the metal other than aluminum; and
- (b) electrolysing the mixture by applying a reducing potential to the substrate, relative to the counter electrode.

* * * * *